(12) United States Patent
Rivero et al.

(10) Patent No.: US 9,089,494 B2
(45) Date of Patent: Jul. 28, 2015

(54) ULTRA-VIOLET INHIBITION SYSTEM

(75) Inventors: Rene Thomas Rivero, West New York, NJ (US); Frank A. Lucia, III, Wantage, NJ (US); Vinod Topiwala, Edison, NJ (US)

(73) Assignee: Coty S.A. (FR)

( * ) Notice: Subject to any disclaimer, the term of this patent is extended or adjusted under 35 U.S.C. 154(b) by 622 days.

(21) Appl. No.: 10/941,037

(22) Filed: Sep. 14, 2004

(65) Prior Publication Data
US 2006/0057080 A1 Mar. 16, 2006

(51) Int. Cl.
| | |
|---|---|
| *A61K 8/18* | (2006.01) |
| *A61K 8/00* | (2006.01) |
| *A61K 8/37* | (2006.01) |
| *A61K 8/35* | (2006.01) |
| *A61Q 17/04* | (2006.01) |

(52) U.S. Cl.
CPC ... *A61K 8/37* (2013.01); *A61K 8/35* (2013.01); *A61Q 17/04* (2013.01); *A61K 2800/88* (2013.01); *A61K 2800/882* (2013.01)

(58) Field of Classification Search
USPC ...................................... 424/59, 60, 400, 401
See application file for complete search history.

(56) References Cited

U.S. PATENT DOCUMENTS

| | | | | |
|---|---|---|---|---|
| 6,048,517 | A * | 4/2000 | Kaplan | 424/60 |
| 6,074,630 | A * | 6/2000 | Devillez et al. | 424/59 |
| 6,485,713 | B1 | 11/2002 | Bonda et al. | |
| 6,555,095 | B1 | 4/2003 | Garrison | |
| 6,746,666 | B1 | 6/2004 | Luther | |
| 2003/0077240 | A1 | 4/2003 | LeGrow et al. | |
| 2003/0103915 | A1 | 6/2003 | Quintini | |
| 2003/0127633 | A1 | 7/2003 | Heidenfelder | |
| 2003/0157039 | A1 | 8/2003 | Ferrero et al. | |
| 2003/0175316 | A1 * | 9/2003 | Pate et al. | 424/401 |
| 2003/0228267 | A1 | 12/2003 | Aust et al. | |

FOREIGN PATENT DOCUMENTS

| | | |
|---|---|---|
| AU | 2004258836 A1 | 2/2005 |
| CA | 2527505 A1 | 2/2005 |
| DE | 19716070 A1 | 10/1998 |
| DE | 19937299 A1 | 2/2001 |
| EP | 6074630 | 6/2000 |
| EP | 6485713 | 11/2002 |
| EP | 1300138 A2 | 4/2003 |
| EP | 6555095 | 4/2003 |
| EP | 20030157039 A1 | 8/2003 |
| EP | 05009341 A2 | 2/2005 |
| EP | 2389921 | 11/2011 |
| JP | 7330563 | 12/1995 |
| JP | 2000505111 | 4/2000 |
| JP | 2001010942 | 1/2001 |
| JP | 2003516330 | 5/2003 |
| JP | 2005523297 | 8/2005 |
| WO | WO-03075877 A2 | 9/2003 |
| WO | WO-2005/009341 A2 | 2/2005 |
| WO | WO-2006031833 A2 | 3/2006 |
| WO | WO-2006031833 A3 | 3/2006 |

OTHER PUBLICATIONS

"European Application Serial No. 05797400.8, Office Action mailed Apr. 7, 2009", 9 pgs.
"European Application Serial No. 05797400.8, Office Action mailed Jul. 29, 2009", 1 pg.
"China Application No. 200580030777.1, Office Action Mailed on Jun. 19, 2009", 6 pgs.
"Australian Aplication No. 2005208712, Examiner Report mailed on Mar. 1, 2010", 2 pgs.
"European Application No. 05797400.8, Office Action Mailed Jan. 26, 2010", 4 pgs.
"International Application Serial No. PCT/US05/32604, International Search Report mailed Sep. 24, 2007", 2 pgs.
"International Application Serial No. PCT/US05/32604, Written Opinion mailed Sep. 24, 2007", 7 pgs.
"Application Serial No. 05797400.8; Office Action Response Filed May 28, 2010", 9 pgs.
"Chinese Application Serial No. 200580030777.1, Office Action mailed Apr. 6, 2010", 5 pgs.
"European Application Serial No. 05797400.8, Office Action mailed on Jun. 22, 2010", 4 pgs.
"Australian Aplication No. 2005284885 , Office Action Mailed on Sep. 15, 2010", 13 pgs.
"Australian Aplication No. 2005284885 , Office Action Response Filed Nov. 18, 2010", 8 pgs.
"Australian Application Serial No. 2005284885, Subsequent Examiner Report mailed Oct. 14, 2010", 3 Pgs.
"European Application Serial No. 05797400.8, Office Action Response Filed on Oct. 19, 2010", 5 pgs.
"European Application Serial No. 05797400.8, Office Action mailed Oct. 28, 2010", 3 pgs.
"European Application Serial No. 057974008.8, Response filed Mar. 3, 2011 to Office Action mailed Oct. 28, 2010", 8 pgs.
"Japanese Application Serial No. 2007-531454, Office Action mailed May 6, 2011", English translation, 2 pgs.
"European Application Serial No. 11175998.1, Partial Search Report Rule 64 mailed Oct. 20, 2011", 6 pgs.
"Japanese Application Serial No. 2007-531454, Response filed Sep. 13, 2011 to Office Action Received May 6, 2011", 11 pgs.
"Canadian Application Serial No. 2,580,465, Office Action mailed Aug. 13, 2012", 4 pgs.
"Canadian Application Serial No. 2,580,465, Response filed Feb. 13, 2013 to Office Action mailed Aug. 13, 2011", 8 pgs.
"European Application Serial No. 11175998.1, Extended Search Report mailed Apr. 25, 2012", 16 pgs.
"Canadian Application Serial No. 2,580,465, Office Action mailed Apr. 22, 2013", 2 pgs.

* cited by examiner

*Primary Examiner* — Mina Haghighatian
*Assistant Examiner* — Luke Karpinski
(74) *Attorney, Agent, or Firm* — Schwegman Lundberg & Woessner, P.A.

(57) ABSTRACT

The invention described herein includes a chemical system consisting essentially of octyl methoxycinnamate, oxybenzone, Ethylhexyl Salicylate, and Avobenzone and optionally, water. The chemical system imparts resistance to ultraviolet energy when added to cosmetic formulations, chemical formulations, and medicinal formulations.

7 Claims, No Drawings

ULTRA-VIOLET INHIBITION SYSTEM

Embodiments of the invention described herein relate to an ultra-violet inhibition system, one or more methods for making the ultra-violet inhibition system and one or more methods for using the ultra-violet inhibition system.

BACKGROUND

Color is the first and most important attribute of a cosmetic product that consumers see prior to their purchase of a cosmetic product. Stability of the color in cosmetic products is impacted by exposure to ultraviolet radiation from one or more artificial light sources as well as from direct sunlight and/or indirect sunlight.

Sunscreens are a recommended form of protection for skin from the damaging effect of ultraviolet radiation emitted by the sun whenever the skin is exposed. Repeated use of sunscreen is necessary for preventing or minimizing sunburn and for allowing a natural tan to develop. Improper use of sunscreens on skin leads to sunburn.

Improper use of sunscreens in cosmetic products leads to damage of the cosmetic product due to ultraviolet light that is analogous to damage of the skin. Ultraviolet light from artificial light, direct sunlight and indirect sunlight distorts color in cosmetics and renders it undesirable to consumers.

Ultraviolet, UV, radiation is defined as that portion of the electromagnetic spectrum between x rays and visible light, between 40 and 400 nm (30-3 eV). The UV spectrum is divided into vacuum UV at 40-190 nm, far UV at 190-220 nm, UVC at 220-290 nm, UVB at 290-320 nm, and UVA at 320-400 nm. The sun is a primary natural source of UV radiation. Artificial sources include black lights, mercury vapor lamps, halogen lights, high-intensity discharge lamps, fluorescent and incandescent sources. Unique hazards apply to the different sources depending upon the wavelength range of the emitted UV radiation. The UVC source of radiation is almost never observed in nature because it is absorbed completely in the atmosphere, as are far UV and vacuum UV.

UVB is typically the most destructive form of UV radiation because it has enough energy to cause photochemical damage and is not completely absorbed by the atmosphere. UVA is the most commonly encountered type of UV light. UVA exposure has an initial pigment-darkening effect that causes tanning on skin. Atmospheric ozone absorbs very little of this part of the UV spectrum. On exposure to UV A-B radiation, atoms of a color compound undergo a change by exiting their electrons to a higher energy level. This electron transition contributes to a discoloration of a cosmetic product.

There have been two basic approaches to inhibit UV light damage in a cosmetic product. One approach has used a physical blocker such as titanium oxide which acts to ward off the UV rays and create a physical blockade against incoming light. This approach is limited to specific types of cosmetics.

Another approach has used a chemical absorber which accepts the UV radiation and converts it into harmless energy such as heat. With most UV-absorbers, the benzene ring or an extended lambda-system is substituted with efficient electron-withdrawing groups. Carbonyl groups are a typical type of withdrawing group. An electron-donating group such as an amino or methoxy group is typically present in a para position to the carbonyl group. The electron-donating group often produces a so-called push/pull substituted conjugated system. This approach does not prevent adverse effects but merely limited adverse effects of UV radiation in cosmetic products.

SUMMARY

One embodiment of the invention described herein includes a chemical system consisting essentially of octyl methoxycinnamate, oxybenzone, Ethylhexyl Salicylate, optionally water, and Avobenzone.

Another embodiment of the invention includes a method for preventing ultraviolet degradation in a chemical composition. The method includes preparing a chemical system consisting essentially of octyl methoxycinnamate, oxybenzone, Ethylhexyl Salicylate, optionally water and Avobenzone; and providing the chemical system to a manufacturer of a chemical composition.

One other embodiment of the invention includes a method for preparing a chemical composition, resistant to ultraviolet degradation, without addition of heat. The method includes obtaining a chemical system comprising octyl methoxycinnamate, oxybenzone, Ethylhexyl Salicylate, and Avobenzone; and adding the chemical system to the chemical composition without an addition of heat.

Another embodiment of the invention includes a method for making a system for preventing ultraviolet degradation in a chemical composition. The method includes preparing a mixture consisting essentially of ultraviolet inhibitors in a powder form, water, and ultraviolet inhibitors in a liquid form; heating the mixture to a temperature of 50 to 55 degrees Centigrade, wherein powder-based components are dissolved in a liquid phase; optionally adding additional powders or liquids to the liquid phase, wherein the liquid phase is a clear to yellowish liquid; and packaging the liquid phase.

DESCRIPTION

Invention embodiments are described in sufficient detail to enable those skilled in the art to practice the invention. Other embodiments may be utilized and structural, logical, chemical, and other changes may be made without departing from the spirit or scope of the invention discussed herein. The following detailed description is, therefore, not to be taken in a limiting sense, and the scope of the invention discussed herein is defined only by the appended claims.

Embodiments of the invention described herein include a base system for use in UV labile compositions to prevent degradation and damage from UV radiation as well as formulations that include the base system, a method for making the base system and a method for blending the base system with a UV labile composition.

The base system includes a blend of UV filters, namely octyl methoxycinnamate, avobenzone, oxybenzone, and octyl salicylate. The concentration of each UV filter and ratio of one filter to another are variable and depend upon the application of the base system. For instance, the concentration of each UV filter are different for each application in a group including blush, concealer, and foundation.

Other components that may be added to the base system include vitamins, such as vitamin A, C, D and E and any other oil soluble vitamins in percentages of 0.001-1.00 percent. Antioxidants such as BHT, Tinosorb (bis-ethylhexyloxyphenol methoxyphenyl triazine), Bis-Benzotriazolyl Tetramethylbutyl Phenol, Tinogard (tris(tetramethylhydroxypiperidinol)citrate, tetradibutyl Pentaerithrityl Hydroxyhydrocinnamate, sodium benzotriazolyl butylphenol sulfonate, Cibafast and other antioxidants known to those skilled in the art may be incorporated into the base system in percentages of 0.001-2.00 percent by weight of the blend.

Other SPF active components that may be added to the base system for some embodiments include titanium oxide, octylcrylene, PABA, benzophenones as well as other SPF agents known to those skilled in the art. These components are added in percentages between 0.001-8.00 percent. These SPF components may be added as a single component for some embodiments, as groups of components for other embodiments.

Active components that contribute to deodorancy such as Farnesol, Triclosan, Deo Safe Active, Zinc Ricinoleate, silver ion, triethyl citrate and other deodorant actives known to those skilled in the art may be added to the base system in percentages between 0.01-1.00 percent by weight of the base system. Other agents such as sequestering agents, chelating agents, preservatives, and anti-nitrosating agents may be added in concentrations ranging from about 0.001-1.00 percent.

For some embodiments, aroma chemicals are incorporated into the blend to provide unique properties that increase performance of a composition. Naturally derived active botanical essential oils and lipid fractions may also be incorporated into the blend to achieve unique appearance and improve performance.

The base system of the invention is usable as a stand alone UV inhibition system for cosmetic formulations, and, for some embodiments, medicinal formulations, and chemical formulations generally, having a susceptibility to UV deterioration. The base system of the invention is also usable as a carrier for additional adjuvants that contribute to the overall stability and efficacy of cosmetic, medicinal and chemical products. These adjuvants include the additional SPF active components, deodorants, and aroma chemicals described herein. The base system is also usable as an SPF cocktail that produces SPF values of 4-50, depending upon the total concentration of the base system that is used in the finished consumer product.

The base system of the invention is prepared by heating liquid components such as octyl methoxycinnamate and octyl salicylate, of the system in a steam jacketed kettle to a temperature range of 50-55 degrees Centigrade. Powder-based components are dissolved in the heated liquid components. All other components are included in an appropriate liquid phase or powder phase and are added separately or in unison.

The base system is a stable, clear to yellowish liquid that may be directly added to a finished product for some embodiments. For other embodiments, the base system is combined in a separate phase to achieve a desired solubility. The base system may be prepared in advance in composition production and may be incorporated at room temperature with no additional heat. The base system imparts stability and improved efficacy to formulations into which it is added. The base system aids in the manufacture of cosmetic formulations by reducing processing time for manufacture. The base system also simplifies manufacture and does not require manufacturers to have sophisticated equipment and knowledge of sophisticated UV cocktails to make a product.

One formulation embodiment of the base system is a water based system having the following ingredients:

| Ingredient | % w/w |
| --- | --- |
| Octyl Methoxycinnamate | 20.00–90.00 |
| Ethylhexyl Salicylate | 1.00–90.00 |
| Avobenzone | 1.00–25.00 |

A lipophillic-based embodiment of the base system includes the following ingredients:

| Ingredient | % w/w |
| --- | --- |
| Octyl Methoxycinnamate | 20.00–90.00 |
| Oxybenzone | 1.00–25.00 |
| Ethylhexyl Salicylate | 1.00–90.00 |
| Avobenzone | 1.00–25.00 |

The base system of the invention is free from solvents and extraction residuals. One other water-based base system includes the following ingredients:

| Ingredient | % w/w |
| --- | --- |
| Octyl Methoxycinnamate | 70.00 |
| Ethylhexyl Salicylate | 15.00 |
| Avobenzone | 15.00 |

Another base system formulation includes the following ingredients:

| Ingredient | % w/w |
| --- | --- |
| Octyl Methoxycinnamate | 60.00 |
| Oxybenzone | 15.00 |
| Ethylhexyl Salicylate | 15.00 |
| Avobenzone | 10.00 |

The cosmetic and dermatological preparations according to the invention may contain cosmetic auxiliaries, such as those customarily used in such preparations, e.g. preservatives, bactericides, perfumes, antifoams, dyes, pigments which have a coloring effect, thickeners, moisturizers and/or humectants, fats, oils, waxes or other customary constituents of a cosmetic or dermatological formulation, such as alcohols, polyols, polymers, foam-stabilizers, electrolytes, organic solvents or silicone derivatives.

Examples of the types of cosmetic products of the invention described herein include soap, body shampoo, facial cleansing cream, and other such cleansing cosmetic products; skin toners, creams, emulsions, packs, and other such basic skin care products; powders, foundations, and other such base makeup products; lipstick, blusher, eye shadow, eye liner, mascara, and other such facial cosmetic products; makeup products for manicures and the like; shampoos, hair rinses, hair conditioners, hair treatments, setting lotions, blow styling lotions, hairsprays, foam styling agents, gel styling agents, hair liquid, hair tonic, hair cream, hair growth tonic, hair growth stimulants, hair dyes, hair dressing, and other such hair care cosmetic products; perfumes, eau de colognes, and other such aromatic cosmetic products; toothpastes; bath preparations; and depilatories, aftershave lotions, antiperspirants, deodorants, sun blocks, and other such special cosmetic products. Basic skin care products, makeup products, and other such skin cosmetic products or hair care cosmetic products are particularly preferred. Examples of the physical states of this cosmetic product include aqueous liquid, oil-based liquid, emulsion, cream, foam, semisolid, solid, and powder. It is also possible to use this cosmetic product by spraying.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

What is claimed is:

1. A liquid blend consisting of octyl methoxycinnamate in a concentration of 70.00 percent by weight, ethylhexyl salicylate in a concentration of 15.0 percent by weight, avobenzone in a concentration of 15.00 percent by weight wherein the liquid blend is used for slowing ultraviolet degradation of a chemical composition with a susceptibility to ultraviolet deterioration when the blend is added to the chemical composition wherein the ultraviolet inhibitor liquid blend is packaged for supply to manufacturers.

2. A method for slowing the rate of ultraviolet degradation in a chemical composition, comprising:
   preparing a chemical liquid blend of ultraviolet inhibitors, the chemical liquid blend consisting essentially of a mixture of octyl methoxycinnamate in a concentration of 70.00 percent by weight, ethylhexyl salicylate in a concentration of 15 percent by weight, avobenzone in a concentration of 15 percent by weight wherein the blend is useful for slowing ultraviolet degradation of a chemical composition and wherein the blend is devoid of any other ultraviolet inhibitors;
   packaging the chemical blend for delivery to a manufacturer of the chemical composition; and
   adding the chemical blend of ultraviolet inhibitors to a chemical composition.

3. The method of claim 2 wherein the manufacturer adds the chemical system to the chemical composition without an addition of heat.

4. A system of ultraviolet inhibitors useful for slowing the ultraviolet degradation of a chemical composition, the system consisting essentially of a liquid mixture of octyl methoxycinnamate in a concentration of 60.0 percent by weight, ethylhexy salicylate in a concentration of 15.00 percent by weight, and avobenzone in concentrations of 10.0 percent by weight and oxybenzone in a concentration of 15.00 percent by weight, wherein the mixture is devoid of any other ultraviolet inhibitors, and packaging for storing and transporting the mixture of ultraviolet filters, wherein the mixture is useful for slowing the ultraviolet degradation of chemical compositions.

5. A method for making a system for slowing ultraviolet degradation in a chemical composition, comprising:
   preparing a mixture of ultraviolet inhibitors in a powder form, water, and ultraviolet inhibitors in a liquid form, wherein the mixture is useful for slowing the ultraviolet degradation of chemical compositions and consists essentially of 60% by weight octyl methoxycinnamate, 15% by weight oxybenzone, 15% by weight ethylhexyl salicylate, and 10% by weight avobenzone and wherein the mixture is devoid of any other ultraviolet inhibitors;
   heating the mixture to a temperature of 50 to 55 degrees Centigrade, wherein powder-based components are dissolved in a liquid phase; and
   packaging the liquid phase to form a system for slowing ultraviolet degradation in a chemical composition.

6. The method of claim 5 wherein the chemical system is a cosmetic formulation.

7. A system for slowing ultraviolet degradation in a chemical composition, produced by the method of claim 5.

* * * * *

UNITED STATES PATENT AND TRADEMARK OFFICE
CERTIFICATE OF CORRECTION

PATENT NO.       : 9,089,494 B2                                             Page 1 of 1
APPLICATION NO.  : 10/941037
DATED            : July 28, 2015
INVENTOR(S)      : Rivero et al.

It is certified that error appears in the above-identified patent and that said Letters Patent is hereby corrected as shown below:

In the Claims

In column 5, line 6, in Claim 1, delete "15.0" and insert --15.00--, therefor

In column 6, line 2, in Claim 4, delete "60.0" and insert --60.00--, therefor

In column 6, line 2-3, in Claim 4, delete "ethylhexy" and insert --ethylhexyl--, therefor In column 6, line 4, in Claim 4, delete "10.0" and insert --10.00--, therefor Signed and Sealed this
Twenty-ninth Day of March, 2016

Michelle K. Lee
*Director of the United States Patent and Trademark Office*